United States Patent [19]

Bartley

[11] Patent Number: 4,628,128
[45] Date of Patent: Dec. 9, 1986

[54] PROCESS FOR THE PREPARATION OF ETHYLENE GLYCOL BY CATALYTIC HYDROGENATION

[75] Inventor: William J. Bartley, Charleston, W. Va.

[73] Assignee: Union Carbide Corporation, Danbury, Conn.

[21] Appl. No.: 697,926

[22] Filed: Feb. 4, 1985

[51] Int. Cl.[4] ..................... C07C 29/136; C07C 31/20
[52] U.S. Cl. .................................. 568/864; 502/243; 568/881; 568/885
[58] Field of Search ......................... 568/864, 881, 885

[56] References Cited

U.S. PATENT DOCUMENTS 4,112,245  9/1978  Zehner et al. ..................... 568/864

*Primary Examiner*—J. E. Evans
*Attorney, Agent, or Firm*—Steven T. Trinker

[57] ABSTRACT

A process for the preparation of ethylene glycol by the vapor phase catalytic hydrogenation of at least one of di(lower alkyl) oxalate and lower alkyl glycolate in the presence of a hydrogenation catalyst comprising a carrier, which catalyst is suitable for the hydrogenation of alkyl oxalate and alkyl glycolate to ethylene glycol, the improvement lies within the preparation of the catalyst by employment of catalysts comprising carriers having specific ranges of physical parameters, including average pore diameter and pore volume, which parameters are interrelated by a relative activity index.

17 Claims, No Drawings

PROCESS FOR THE PREPARATION OF ETHYLENE GLYCOL BY CATALYTIC HYDROGENATION

This invention relates to an improved process for the preparation of ethylene glycol by the vapor phase catalytic hydrogenation of at least one of di(lower alkyl) oxalate and alkyl glycolate in the presence of a hydrogenation catalyst comprising a carrier, which catalyst is suitable for the hydrogenation of alkyl oxalate and alkyl glycolate to ethylene glycol. More particularly, this invention relates to the catalytic hydrogenation of di(-lower alkyl) oxalate to produce ethylene glycol using catalysts comprising carriers having specific ranges of physical parameters, including average pore diameter and pore volume, which parameters are interrelated by a relative activity index.

INTRODUCTION TO ETHYLENE GLYCOL

Ethylene glycol is a valuable commercial chemical and finds application in deicing fluids, antifreeze, hydraulic fluids, manufacture of alkyd resins, solvents and the manufacture of polyesters. As disclosed in Kirk-Othmer, Encyclopedia of Chemical Technology, 3rd Edition, ethylene glycol is commercially made by the hydrolysis of ethylene oxide which in turn is made by the catalytic epoxidation of ethylene using air or oxygen. However, several problems, particularly raw material supply, are associated with these commercial processes.

First, ethylene is made commercially from natural gas liquids or naphthas. Second, in the catalytic epoxidation of ethylene in commercial facilities, the selectivity to ethylene oxide is usually less than 80 percent, with carbon dioxide being the primary by-product. Finally, the hydrolysis of ethylene oxide to ethylene glycol in conventional processes coproduces diethylene glycol and triethylene glycol.

It has been proposed to use synthesis gas, i.e., mixtures of carbon monoxide and hydrogen, as alternative starting materials for the preparation of ethylene glycol, thus reducing dependency on ethylene and in turn the feed stocks required to produce ethylene. In some of these processes, the synthesis gas is reacted to form di(alkyl) oxalates which are then hydrogenated to form the desired ethylene glycol. This hydrogenation is especially difficult since the hydrogenation must be sufficient to reduce the ester radical, yet avoid over hydrogenation of glycol and/or intermediate glycolates to ethanol and other by-products. Moreover, it can be readily appreciated that hydrogenation reactions can yield a spectrum of products, due to both under and over hydrogenation. These by-products not only reduce the efficiency to ethylene glycol, but also can present troublesome impurities that must be removed from the ethylene glycol.

U.S. Pat. No. 4,112,245 to Zehner, et al., discloses the preparation of ethylene glycol by the vapor phase catalytic hydrogenation of dialkyl oxalate in the presence of a copper-containing catalyst. However, this patent does not disclose any significance to the physical parameters of the carrier material. In fact, this patent only refers to supported catalysts in vague, general terms without explaining what is meant by the term supported catalyst. The patent gives no examples of supported catalysts, with the possible exception of nickel on kieselguhr, in which kieselguhr is active in the reaction and not an inert carrier or support material.

INTRODUCTION TO CATALYST CARRIERS

It is often desired to employ catalysts that comprise carriers. Among the benefits that are provided by catalyst carriers are reducing the amount of the catalytically-active species required, providing the catalyst in a more easily handled form, and facilitating the use of the catalyst in commerical-sized reactors without, for example, undue pressure drops or poor distribution of reactants throughout the reaction bed.

Carriers are available in many sizes, shapes and compositions. Moreover, the surface and internal structures of carriers can vary widely. Unfortunately, with many reactions the nature of the carrier can affect the performance of the catalyst. The selection of suitable carriers has thus proven to be an empirical and complex task. The literature relating to carrier selection is often couched in generalities because of the empiric characteristic of the art.

For instance, Rhone-Poulenc Chemical Company Catalog (p. 4), Technical Documentation, SC-MIN. S-81-1-3, entitled "Spherulite Catalyst Carriers" discloses that an increase in carrier surface area may lead to an increase in reaction velocity; however, diffusional limitations can occur when too small pores are used. The presence of large pores enables a more rapid distribution of the reactants and are often used in combination with smaller pores. While this publication generally discloses some physical parameters of carriers, it does not specifically disclose processes that would benefit from these physical parameters.

A. Wheeler, "Reaction Rates and Selectivity in Catalyst Pores", in *Catalysis* Vol. II, p. 105, P. H. Emmett, (Ed.) (1955), Rheinhold, N.Y.; discloses that the carrier contans a network of interconnecting very fine pores and provides the seat of catalytic activity. The total surface area, distribution of pore sizes and total pore volume can be determined by routine methods. Wheeler states that pore size, pore volume and carrier size determine the degree to which diffusion affects reaction rates. This reference does not, however, disclose any specific physical parameters for carriers utilized in the hydrogenation of di(lower alkyl) oxalate to ethylene glycol.

Harshaw Catalyst Catalog, (p. 43–45), (1980), entitled "Transport in Solid Catalysts", discloses that the rate of physical transport of reactants to the catalyst surface must keep up with the rate of the chemical reaction at the surface in order to effectively use the surface area of the catalyst. Since transport of reactants through narrow pores is of necessity low, there is a limit to the size of the pores, and, hence, to the size of the particles and the surface area per unit volume, unless wide pores can be realized together with very small particles. However, this publication states that the "initial selection of a catalyst is still based on trial and error."

Thus, while the prior art has in general terms recognized the importance of the physical parameters of carriers, there has been a general failure in the prior art to interrelate these physical parameters, especially in reference to particular catalytic reactions, and certainly no guidance has been provided toward selecting advantageous catalysts for the hydrogenation of di(lower alkyl) oxalates to prepare ethylene glycol.

SUMMARY OF THE INVENTION

This invention relates to a process for the preparation of ethylene glycol comprising the steps of contacting, in the vapor phase and under glycol-forming hydrogenation conditions, hydrogen with at least one of di(lower alkyl) oxalate and lower alkyl glycolate in the presence of a catalytically-effective amount of a hydrogenation catalyst comprising a carrier, which catalyst is suitable for the hydrogenation of alkyl oxalate and alkyl glycolate to ethylene glycol, wherein the carrier is characterized by a relative activity index of at least about 1.0, said relative activity index being defined by the formula, relative activity index $= 1.38 + 0.39a + 0.76b + 0.001c + 0.35d - 0.39ab + 0.012bc + 0.003cd$, wherein a is defined as the nominal external surface area of a typical carrier particle (S), expressed in square millimeters per particle units, divided by the volume (V) of the same carrier particle, expressed in cubic millimeters per particle units, minus 1.96 ((S/V)−1.96); b is defined as the pore volume (P) of the carrier, expressed in cc/gram units, minus 0.84 (P−0.84); c is defined as the average pore diameter (D), expressed in Angstrom units, minus 169 (D−169); and d is defined as the macroporosity variable (M) minus 0.24 (M−0.24), wherein the macroporosity variable is assigned a value of 1.0 if said carrier has at least about 20% of its pore volume associated with pores having a diameter of at least about 1000 Angstroms, and a value of zero if said carrier has less than about 20% of its pore volume associated with pores having a diameter of at least about 1000 Angstroms.

In addition, this invention relates to a hydrogenation catalyst comprising a carrier, said catalyst being suitable for the hydrogenation of alkyl oxalate and alkyl glycolate to ethylene glycol, wherein the carrier is characterized by a relative activity index of at least about 1.0.

Catalysts having carriers with a relative activity index of at least about 1.0 can exhibit significantly more activity toward ethylene glycol than those produced from carriers whose relative activity index is substantially below about 1.0.

DISCUSSION OF THE HYDROGENATION PROCESS

Ethylene glycol can be prepared by the vapor phase catalytic hydrogenation of a di(lower alkyl) ester of oxalic acid at elevated temperature and pressure.

An overall equation for the reaction is believed to be represented as follows:

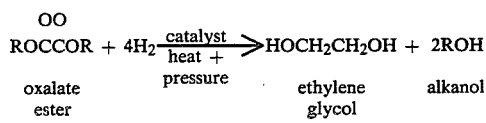

oxalate ester — ethylene glycol — alkanol

The hydrogenation of di(alkyl) oxalates is believed to proceed stepwise according to the following equations:

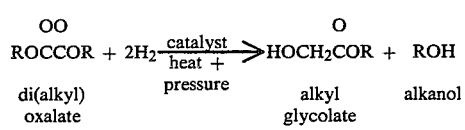

di(alkyl) oxalate — alkyl glycolate — alkanol

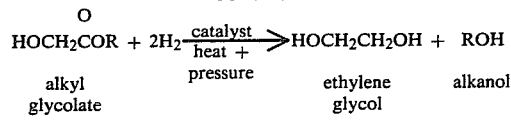

alkyl glycolate — ethylene glycol — alkanol

The first step involves the hydrogenation of one of the alkoxycarbonyl groups of a di(alkyl) oxalate to form an alkyl glycolate and the corresponding alkanol. In the second step, the remaining alkoxycarbonyl group is hydrogenated to produce ethylene glycol plus the corresponding alkanol.

The oxalate esters which may be hydrogenated in accordance with the processes of this invention conform to the general formula:

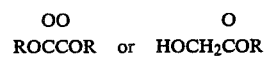

wherein R is a lower alkyl group. The preferred esters for use in the hydrogenation process for the preparation of ethylene glycol are those esters wherein R is an alkyl group containing from 1 to 4 carbon atoms. Especially preferred are dimethyl oxalate and diethyl oxalate.

In carrying out the hydrogenation reaction, the di(lower alkyl) ester of oxalic acid is generally preheated and vaporized, with the conditions of the hydrogenation being selected to ensure that essentially all of the ester is in the vapor state when passed over the catalyst bed. Thus, the reaction zone is maintained at an elevated temperature and pressure sufficient for hydrogenation to ethylene glycol and for preventing condensation of the oxalate ester and the product ethylene glycol.

The processes, in accordance with the present invention, are carried out by passing vaporized oxalate ester, together with hydrogen, over the catalyst maintained at a reaction zone temperature typically between about 150° C. and about 300° C. and preferably between about 180° C. and about 240° C. The molar ratio of hydrogen to oxalate ester passed to the reaction zone is usually at least sufficient on a stoichiometric basis for complete hydrogenation of the oxalate ester to ethylene glycol and is often between about 4:1 and 200:1 and preferably between about 10:1 and 100:1. A hydrogen pressure between about 1 bar and about 350 bars is frequently used and preferably the hydrogen pressure is between about 10 bars and about 100 bars. In advantageous aspects of the processes, the gas hourly space velocity (the total volume of the vaporous oxalate and hydrogen gaseous mixture, as calculated at ambient temperature and pressure, passed over a unit volume of hydrogenation catalyst bed per hour) is between about 2,000 hr.$^{-1}$ and about 25,000 hr.$^{-1}$ and preferably between about 5,000 hr.$^{-1}$ and about 15,000 hr.$^{-1}$. The liquid hourly space velocity of oxalate ester (calculated as the liquid volume of oxalate, expressed in liquid form per unit volume of hydrogenation catalyst which is passed over the catalyst) is typically maintained between about 0.1 hr.$^{-1}$ and about 3.0 hr.$^{-1}$ and preferably between about 0.5 hr.$^{-1}$ and about 2.0 hr.$^{-1}$. For convenience, as used herein, the oxalate liquid hourly space velocity is calculated prior to mixing with hydrogen and is based on a liquid rather than a gaseous volume.

In particularly attractive aspects of this invention, the percent conversion, calculated as the moles of oxalate in the feed minus the moles of oxalate recovered in the feed mixture after reaction divided by the moles of oxalate in the feed multiplied by 100, is maintained at greater than about 80% and preferably greater than about 95%. The percent conversion is a dependent variable, as the reaction temperature, the liquid hourly space velocity and other reaction variables are provided at sufficient interrelated values to obtain the desired conversion percent.

CATALYST AND ITS PREPARATION

The catalytically-active moieties deposited on the carrier may, in the broadest sense, include any moiety or mixture of moieties, capable of selectively hydrogenating esters to form hydroxyl substituted carbons such as the hydrogenation of di(alkyl) oxalate to form ethylene glycol. Therefore, a moiety exhibiting a relatively weak hydrogenation activity is preferred in order to maximize ethylene glycol production and minimize hydrogenolysis of the ethylene glycol. Most often, the hydrogenation catalyst comprises copper, either in the elemental form or combined with oxygen. Other representative moieties may include, for example, nickel, cobalt, ruthenium, palladium, platinum, rhodium, rhenium and combinations thereof. Preferred catalysts are the copper-containing catalysts, both unpromoted and promoted with components (e.g., metal oxide) containing chromium, manganese and/or zinc. The amount of catalytically-active moiety, based on total weight of the catalyst, is generally from about 1 to 50%, while a range of about 2 to 20% is preferred, and about 5 to 15% being more preferred.

Carriers are usually porous substances on which the catalytically-active component is deposited. Most preferably, the carriers are substantially inactive or inert. Suitable carriers may comprise one or more of silica, alumina, titania, molecular sieves, diatomaceous earth, activated carbon, silicon carbide, pumice, zeolite and the like. The silica, titania and alumina carriers are preferred, and the silica carrier is especially preferred.

Carriers can be categorized by their chemical composition and physical properties. The carriers used in accordance with this invention are often characterized by physical properties such as (a) pore volume, (b) average pore diameter, (c) carrier geometry (the nominal external surface area and volume of the carrier), and (d) pore-size distribution.

The terms surface area and nominal external surface area are distinct and should not be confused. Surface area constitutes the total surface area of the carrier including the surface area of the carrier's interconnecting pores. The nominal external surface area is the calculated superficial surface area of the carrier, i.e., a smooth surface devoid of pores. The nominal external area directly affects the relative activity index. Although the internal surface area is important to catalytic activity, this parameter does not appear in the relative activity index formula. However, the magnitude of the internal surface area is determined by the pore volume and average pore diameter terms, which are included in the relative activity index formula.

In general, a carrier having a high surface area is desired to obtain a high dispersion of the catalytically-active moiety on the surface of the carrier. Typically, the reaction rate increases as the dispersion of the catalytically-active moiety increases. However, a high surface area is obtained at the sacrifice of pore size (average pore diameter), and this sacrifice may be disadvantageous to activity if the reaction is diffusionally limited. Therefore, with surface area, a compromise or upper limit is typically established. Surface areas desirably range from at least about 50 $m^2$/gram to about 600 $m^2$/gram. Preferred surface areas typically range from about 75 $m^2$/gram to about 400 $m^2$/gram, with surface areas ranging from about 100 $m^2$/gram to about 300 $m^2$/gram being even more preferred. Several other carrier physical parameters have optimum ranges because they are similarly influenced or limited by other physical parameters. The relative activity index interrelates the effects of these physical parameters on oxalate hydrogenation activity.

The pore volume of the carrier, i.e., the total volume of all pores, can affect both the catalyst preparation and the subsequent hydrogenation reaction. Typically, high pore volumes permit higher metal loadings to be achieved without the necessity of multiple impregnation treatments. In preparing impregnated catalysts, the volume of solvent employed often is chosen to be just sufficient to fill the pores. The larger this pore volume, the greater the quantity of catalyst precursor which can be introduced. For the same reason, a high pore volume is useful when the catalyst precursor has a relatively low solubility in the impregnation medium. Generally, a high pore volume results in higher catalyst productivities than otherwise will be obtained. In accordance with this invention, pore volumes, expressed in cc/gram units, desirably range from about 0.4 cc/gram to about 1.5 cc/gram. Preferred pore volumes typically range from about 0.7 cc/gram to about 1.5 cc/gram, with pore volumes ranging from about 0.9 cc/gram to about 1.5 cc/gram being more preferred.

Average pore diameter is inversely related to the total surface area of the carrier, i.e., for a given porosity, the smaller the average pore diameter, the higher the surface area. In accordance with this invention, average pore diameters, expressed in Angstrom units, desirably range from about 25 to about 600 Angstroms. Preferred average pore diameters typically range from about 50 to about 600 Angstroms, with average pore diameters ranging from about 125 to about 600 Angstroms being more preferred.

The geometry of the carrier is also important for catalysts used in processes in accordance with this invention. Advantageously, the carriers are as small as practical. However, when supported catalysts are used in a tubular reactor, the carriers are generally restricted to a minimum diameter to avoid an unacceptably high pressure drop across the catalyst bed. The minimum acceptable diameter will, in general, be a function of the diameter of the tubular reactor and the gas flow rate among other things.

The effect of the carrier on the hydrogenation processes of this invention can be influenced by the shape of the carrier as well as its size. These geometric shapes include spheres, cylinders, cored tablets (also referred to as annular shapes), stars, ribbed extrudates and saddles.

As noted above, the carriers useful in accordance with this invention can be defined in terms of a relative activity index which interrelates the previously discussed physical parameters of pore volume, average pore diameter, pore size distribution, nominal external surface area and volume of the carrier. In accordance with this invention, the hydrogenation catalyst activity may be substantially increased by employing a carrier characterized by a relative activity index of at least about 1.0. A relative activity index greater than about 1.25 is preferred, with an index greater than about 1.50 being more preferred.

In this relationship, the nominal external surface area of the carrier (S) does not include the surface area of internal pores, which contribute most to a carrier's active surface area, e.g., where the catalyst precursor is deposited during impregnation. This nominal external surface area is the calculated superficial surface area, i.e., a smooth surface devoid of any pores. The volume of the carrier (V) is the calculated total volume, and is not to be confused with the pore volume or porosity of the carrier. The nominal external surface area of the carrier, expressed in square millimeters per particle units, to carrier volume, expressed in cubic millimeters per particle units, ratio desirably ranges from about 0.5 to 5.0 $mm^{-1}$. Preferred ratios typically range from about 0.75 $mm^{-1}$ to about 5.0 $mm^{-1}$, with ratios ranging from about 1.0 $mm^{-1}$ to about 4.0 $mm^{-1}$ being more preferred.

The nominal external carrier surface area to carrier volume ratio, (a) in the above-stated relative activity index formula, may be calculated for carriers of varying sizes and shapes. For example, this ratio (a) can be determined by geometric calculation techniques.

The macroporosity variable typically indicates whether a carrier has a significant distribution of macropores. In accordance with this invention, macropores are generally defined as pores having a diameter of at least about 1000 Angstroms. The macroporosity variable, in accordance with this invention, is assigned a value of 1.0 if the carrier has at least about 20% of its pore volume associated with pores in the macropore range. A value of zero is assigned to those carriers having less than about 20% of its pore volume associated with pores in the macropore range.

Preparation of the supported catalyst, in accordance with this invention, typically involves several steps: (1) washing the carrier, (2) impregnating/coating the precursor(s) of the catalytically-active moieties on the carrier, (3) drying and/or calcining the impregnated carrier and (4) reducing the precursor of the catalytically-active moiety to its active form.

Frequently, it is desirable to pretreat the carrier, e.g., by washing to remove significant amounts of extraneous leachable components that may be deleterious to the performance of the catalyst. Conveniently, the washing may be with an acid solution. Any suitable acid treatment (washing) technique may be utilized. An especially preferred acid for the treatment is oxalic acid. Variations of this treatment may be used to accomplish this purpose. The washing is generally sufficient to enhance the performance of the catalyst. It is thought that the washing effects the removal of at least a portion of the leachable iron and/or sulfur from the carrier. See, for example, co-pending U.S. application Ser. No. 697,927, filed on even date herewith by W. J. Bartley, which is herein incorporated by reference. That application discloses a hydrogenation process for the preparation of ethylene glycol from oxalate ester, in which the carrier has a leachable iron ($Fe^{+2}$ and/or $Fe^{+3}$) content not greater than about 0.03%.

Any means of depositing the catalytic metal components on the carrier, e.g., impregnating or coating techniques, may be used. Any effective impregnation treatment or solute may be utilized to impregnate the carrier. Typically, the carrier is impregnated with a medium containing a precursor which is decomposable to the catalytically-active moiety in the final catalyst. Thus, for example, where the desired active moiety is copper, a copper salt, such as copper nitrate, or a copper complex, such as a copper ammonia complex, may conveniently be used as the solute, and then the precursor can be converted to the desired active moiety. Where the desired active material is a material other than copper, a decomposable salt of the desired metal is chosen as the solute of the impregnating solution. In general, the desired active moiety is a metal, or a mixture of metals, and the solute or decomposable compound is correspondingly a metal salt, metal oxide or metal hydroxide or a mixture of metal salts, oxides or hydroxides.

Performance of the supported catalyst may be affected by the nature of the impregnating solution. As described in copending U.S. application Ser. No. 697,928, filed on even date herewith by W. J. Bartley, which is herein incorporated by reference, a catalyst for the preparation of ethylene glycol with a copper-containing catalyst is prepared by contacting said carrier with a copper ammonium carbonate complex medium and reducing the catalytically-active copper moiety to its active copper form.

After impregnation, the carrier with deposited catalytically-active moiety or precursor can be dried, or, if a decomposable precursor is used, it can be converted to the desired catalytically-active form. Usually, drying and decomposition are separate operations, since most decomposable precursors will not be decomposed under normal drying conditions. Drying typically can be accomplished by exposure to drying conditions including elevated temperatures ranging from about 50° C. to about 200° C. for several hours, e.g., 0.5 to 30 hours, with temperatures ranging from about 75° C. to about 150° C. being preferred.

In some instances, when the decomposable precursor is a salt, it may be desired to form the oxide by calcination to facilitate the formation of the metal (should that be the desired catalytically-active moiety) through reduction. Calcination involves high temperature heating under oxidizing conditions so that any hydrates, carbonates, or the like are decomposed and volatile material is expelled. Calcination in an air atmosphere is a preferred means of converting most decomposable precursors to the oxide of the metal. The calcination treatment will usually depend on the decomposable precursor. For example, a copper salt, such as copper nitrate, begins decomposing to the copper oxide at about 170° C. Copper carbonate, on the other hand, does not begin to decompose until a temperature of about 200° C. In general, calcination typically can be carried out by exposure to temperatures ranging from about 170° C. to about 600° C., depending on the catalyst precursor, for a time sufficient to allow substantial conversion to the metal oxide form, with temperatures in the range of about 200° C. to about 500° C., being preferred.

Where the desired catalyst has a metal rather than a metal oxide as its catalytically-active moiety, the catalyst may then be reduced to the metal form by treatment with hydrogen prior to hydrogenation or during the hydrogenation reaction. Other reducing agents, e.g., carbon monoxide and metal hydrides, can also be employed. Reduction prior to the hydrogenation reaction typically involves purging the catalyst with an inert gas to remove oxygen and reducing under conditions that include the presence of reducing agent and elevated temperatures.

Actual reduction procedures will vary depending on the catalyst and catalytically-active moiety. Hydrogen reductions of copper oxide to copper metal are typically carried out at temperatures ranging from about 100° C. to about 300° C. with hydrogen partial pressures ranging from about 0.001 to about 100 bars in the substantial absence of oxygen. A slow reduction time is preferred and therefore preferred temperatures range from about 150° C. to about 250° C. with preferred hydrogen partial pressures ranging from about 0.01 to about 10 bars. Conditions sufficient to convert at least a major portion of the oxide to the metal are preferred, with a conversion of 90% or greater being more preferred.

The following examples are provided to illustrate the present invention in accordance with the principles of this invention, but are not to be construed as limiting the invention.

EXAMPLES

The following discloses the general method employed to prepare and evaluate the catalysts designated in the examples.

1. PREPARATION OF SUPPORTED SILICA CATALYSTS

The carriers are washed by slowly and continuously passing a mixture of oxalic acid, glycerine, and water in proportions of 1:1.5:1.1 by weight, respectively, through a loosely packed bed of carrier contained within a glass column which drains through a stopcock at its base. The contents of the column are maintained at about 90° C. throughout the washing procedure. About 10–20 volumes of the solution containing oxalic acid are used to wash one volume of carrier (loosely packed volume) over a five to fifteen-hour period. The carrier material is then washed with about 20–30 volumes of distilled water at about 90° C. over a period of about five to fifteen hours and then dried overnight at about 110°–150° C. in a drying oven.

The carriers are then impregnated. The desired quantities of copper precursor, $CuCO_3$ (basic), calculated to yield a 10% copper concentration in the finished catalyst, are dissolved in an aqueous $NH_4OH$ medium. The volume of $NH_4OH$ is selected to at least fill the pores and to provide a 4 to 1 molar ratio of ammonia to copper. This mixture is allowed to stand at room temperature (about 20° C.) with occasional stirring until most of the solids are dissolved (about 1 to 60 minutes). Heating to 40°–50° C. may be required to dissolve all solids when high copper concentrations are employed.

The carrier is then placed in a vacuum flask. The top of the flask is sealed with a rubber septum, and the flask is evacuated through the side arm. A syringe needle is then used to inject the impregnating solution onto the evacuated carrier material. When the addition is complete, the material is mixed well, then the impregnated carrier is allowed to stand with occasional stirring at ambient pressure (about 1 atmosphere) for approximately 30 minutes at room temperature. It is then dried in a nitrogen atmosphere using the following heat sequence: 85° C. (for 1 hr.); 110° C. (for 2 hrs.); and 150° C. (for 2 hrs). The impregnated carrier is then calcined at 300° C. for 2 hrs. in an air atmosphere.

To achieve reduction of the copper component, the dried, impregnated carrier is placed in the reactor used for the production of ethylene glycol and heated to 150° C. for 1 hour under flowing nitrogen. Hydrogen is then introduced into the nitrogen stream at a flow rate sufficient to give an atmosphere of about 1–2% hydrogen and a total hydrogen and nitrogen space velocity of about 2000–3000 hr.$^{-1}$ (based on the volume of the catalyst bed). The temperature is increased gradually from 150° C. to 225° C. over an 18-hour period (approximately a 4° C. increase per hour) and then held at 225° C. for 6 hours.

2. PRODUCTION OF ETHYLENE GLYCOL

The hydrogenation of diethyl oxalate is conducted under continuous conditions in a ¾ inch outside diameter by 16 inch stainless-steel tubular reactor (70 milliters volume) which is coaxially fitted with a ⅛ inch diameter stainless-steel thermocouple well in accordance with the following procedure. A 20 ml charge of catalyst is dispersed with an equal volume of 3/32 inch glass helices and placed in the center of the stainless steel tube reactor with beds of 3/32 inch glass helices fully occupying the space above and below the charged catalyst. After reduction, the temperature and molecular hydrogen flow rate are then adjusted to levels set forth in Table 2 and diethyl oxalate flow is started. Liquid diethyl oxalate is premixed and vaporized with molecular hydrogen at 225° C. in a separate preheater filled with 3/32 inch glass helices and of outside dimensions identical to that of the stainless steel tubular reactor, but with an internal volume of 35 ml. The gaseous reactants are then passed downward over the catalyst bed at conditions of temperature, pressure, and gas and liquid flow rates (gas hourly space velocity and liquid hourly space velocity) as indicated in the examples in the table below. The products are then condensed and collected at reactor pressure. The condensate is analyzed by gas chromatography.

In the examples shown in Table 2, the results of catalytic hydrogenations using carriers having a relative activity index of at least about 1.0 (Examples 1 to 24) are compared with those having a relative activity index below at least about 1.0 (Examples C-1 to C-6). The physical characteristics of the carriers utilized in Table 2 are given in Table 1 below.

TABLE 1

| | PHYSICAL CHARACTERISTICS OF CARRIERS USED TO MAKE CATALYSTS | | | | | | |
|---|---|---|---|---|---|---|---|
| Example | Supplier | Carrier (1) | Pore Volume (cc/gram) | Surface Area (m$_2$/g) | Average Pore Diameter (A°) | Pellet Size (diameter by height, mm) (2) | Macroporosity Variable (3) |
| C-1 | Davison | SMR 7-6230-1 | 0.91 | 345 | 65 | 4.8 × 4.6 | 0 |
| C-2 | Davison | SMR 7-6230-2 | 0.54 | 140 | 155 | 4.9 × 4.7 | 0 |
| C-3 | Davison | SMR 7-6230-3 | 0.81 | 370 | 90 | 4.9 × 5.6 | 0 |
| C-4 | Davison | SMR 7-6245-2 | 0.57 | 140 | 162 | 4.9 × 5.3 | 0 |
| 1 | Norton | HSA-15865 | 1.20 | 232 | 207 | 4.2 × 6.5 | 0 |
| 2 | Norton | HSA-15983 | 1.04 | 186 | 223 | 4.3 × 4.6 | 0 |
| 3 | Norton | HSA-16018 | 0.97 | 214 | 182 | 4.3 × 4.6 | 0 |
| C-5 | Davison | SMR 7-6245-2 | 0.57 | 140 | 162 | 4.9 × 5.3 | 0 |
| 4 | Norton | HSA-15865 | 1.20 | 232 | 207 | 4.2 × 6.5 | 0 |
| 5 | Norton | HSA-16018 | 0.97 | 214 | 182 | 4.3 × 4.6 | 0 |
| 6 | Norton | HSA-15865 | 1.20 | 232 | 207 | 1.9 | 0 |

TABLE 1-continued

PHYSICAL CHARACTERISTICS OF CARRIERS USED TO MAKE CATALYSTS

| Example | Supplier | Carrier (1) | Pore Volume (cc/gram) | Surface Area (m$_2$/g) | Average Pore Diameter (A°) | Pellet Size (diameter by height, mm) (2) | Macroporosity Variable (3) |
|---|---|---|---|---|---|---|---|
| 7 | Davison | Grade -59 | 1.08 | 456 | 95 | 1.9 | 0 |
| 8 | United Cat. | T-2085 | 0.49 | 112 | 176 | 1.9 | 1 |
| 9 | Davison | SMR 7-6245-2 | 0.57 | 140 | 162 | 1.9 | 0 |
| 10 | Calcicat | K-361B | 0.77 | 95 | 322 | 1.9 | 0 |
| 11 | United Cat. | L-1259 | 0.53 | 144 | 146 | 1.9 | 1 |
| 12 | Davison | SMR 7-6230-2 | 0.54 | 140 | 155 | 1.9 | 0 |
| 13 | Davison | Grade -59 | 1.08 | 456 | 95 | 1.9 | 0 |
| 14 | Davison | Grade -59 | 1.08 | 456 | 95 | 1.9 | 0 |
| 15 | Davison | SMR 7-6204-2 | 0.65 | 122 | 213 | 1.9 | 0 |
| C-6 | United Cat. | K-361D | 0.76 | 42 | 712 | 3.1 × 3.3 | 0 |
| 16 | United Cat. | L-1259 | 0.52 | 144 | 146 | 3.1 × 6.9 | 1 |
| 17 | United Cat. | T-2085 | 0.49 | 112 | 176 | 3.2 × 7.6 | 1 |
| 18 | United Cat. | T-869 | 0.55 | 68 | 328 | 3.3 × 7.5 | 1 |
| 19 | United Cat. | T-869 | 0.55 | 68 | 328 | 3.3 × 7.5 | 1 |
| 20 | Calcicat | K-361B | 0.77 | 95 | 322 | 3.1 × 3.1 | 0 |
| 21 | Calcicat | K-361B | 0.77 | 95 | 322 | 3.1 × 3.1 | 0 |
| 22 | Fuji-Davison | FD 80518 | 1.00 | 127 | 316 | 2.5 | 0 |
| 23 | Davison | D-59 | 1.08 | 456 | 95 | 5.2 | 0 |
| 24 | Fuji-Davison | FD 80518 | 1.00 | 127 | 316 | 2.5 | 0 |

(1) The physical properties of pore volume, surface area and average pore diameter were determined by utilizing a method similar to ASTM-D-4284 entitled Method for Determination of the Pore Volume Distribution of Catalysts by Mercury Intrusion Porosimetry (1984 Annual Book of ASTM Standards) before the catalyst carriers were given the washing treatment. The letter and numerical designations are the suppliers' identifications.
(2) The average of 10 pellets measured by a micrometer. The diameter by height pellet sizes are cylinders; the others are spheres.
(3) Macroporous carriers = 1, non-macroporous carriers = 0.

TABLE 2

COMPARISON OF CATALYTIC HYDROGENATIONS ACCORDING TO PHYSICAL CHARACTERISTICS OF CATALYST CARRIERS (1)

| Example | Carrier (2) | Temp. (°C.) (3) | H$_2$/DEO (4) | LHSV (hr.$^{-1}$) (5) | GHSV (hr.$^{-1}$) (6) | % DEC CONV. (7) | EG STY (8) | R.A.I. (9) |
|---|---|---|---|---|---|---|---|---|
| C-1 | SMR 7-6230-1 | 210 | 61 | 0.76 | 7600 | 85 | 229 | 0.98 |
| C-2 | SMR 7-6230-2 | 210 | 86 | 0.55 | 7800 | 90 | 152 | 0.76 |
| C-3 | SMR 7-6230-3 | 211 | 84 | 0.56 | 7700 | 92 | 181 | 0.96 |
| C-4 | SMR 7-6245-2 | 210 | 73 | 0.55 | 6500 | 99 | 210 | 0.74 |
| 1 | HSA-15865 | 215 | 48 | 1.0 | 7900 | 99.9 | 404 | 1.57 |
| 2 | HSA-15983 | 210 | 47 | 1.0 | 7800 | 99.8 | 396 | 1.41 |
| 3 | HSA-16018 | 211 | 50 | 0.9 | 7300 | 99.9 | 362 | 1.22 |
| C-5 | SMR 7-6245-2 | 210 | 76 | 0.51 | 6350 | 99.8 | 200 | 0.74 |
| 4 | HSA-15865 | 212 | 51 | 0.88 | 7400 | 99.8 | 342 | 1.57 |
| 5 | HSA-16018 | 212 | 52 | 0.87 | 7200 | 99.7 | 337 | 1.22 |
| 6 | HSA-15865 | 213 | 47 | 1.0 | 7800 | 99.9 | 450 | 2.03 |
| 7 | Grade -59 | 209 | 46 | 1.0 | 7750 | 99.9 | 417 | 1.59 |
| 8 | T-2085 | 210 | 42 | 1.1 | 7600 | 100 | 456 | 1.99 |
| 9 | SMR 7-6245-2 | 210 | 43 | 1.1 | 7650 | 100 | 444 | 1.69 |
| 10 | K-361B | 210 | 45 | 1.0 | 7600 | 100 | 418 | 1.65 |
| 11 | L-1259 | 210 | 38 | 1.2 | 7650 | 100 | 518 | 2.03 |
| 12 | SMR 7-6230-2 | 211 | 47 | 1.0 | 7700 | 100 | 426 | 1.71 |
| 13 | Grade -59 | 208 | 47 | 1.0 | 7700 | 100 | 416 | 1.59 |
| 14 | Grade -59 | 210 | 47 | 1.0 | 7650 | 100 | 417 | 1.59 |
| 15 | SMR 7-6204-2 | 212 | 49 | 0.95 | 7600 | 100 | 410 | 1.61 |
| C-6 | K-361D | 211 | 85 | 0.55 | 7600 | 99.9 | 222 | 0.89 |
| 16 | L-1259 | 212 | 53 | 0.88 | 7600 | 99.8 | 343 | 1.22 |
| 17 | T-2085 | 212 | 51 | 0.88 | 7300 | 99.6 | 270 | 1.14 |
| 18 | T-869 | 211 | 61 | 0.74 | 7400 | 99.8 | 292 | 1.10 |
| 19 | T-869 | 212 | 65 | 0.70 | 7300 | 99.9 | 266 | 1.10 |
| 20 | K-361B | 213 | 70 | 0.63 | 7000 | 99.8 | 237 | 1.16 |
| 21 | K-361B | 212 | 60 | 0.74 | 7200 | 99.8 | 280 | 1.16 |
| 22 | FD 80518 | 214 | 42 | 1.1 | 7700 | 99.8 | 466 | 1.88 |
| 23 | D-59 | 210 | 46 | 0.6 | 4550 | 100 | 236 | 1.01 |
| 24 | FD 80518 | 210 | 48 | 1.2 | 9100 | 99.8 | 474 | 1.74 |

(1) 10% copper catalysts, 450 bars pressure.
(2) The letter and numerical designations are the suppliers' identification. The suppliers can be identified by Table 1.
(3) Reaction zone temperature.
(4) Mole ratio of hydrogen (H$_2$) to diethyl oxalate.
(5) Liquid hourly space velocity.
(6) Gas hourly space velocity.
(7) Percent diethyl oxalate reacted.
(8) Ethylene glycol, space time yield, (grams ethylene glycol/liter catalyst/hour).
(9) Relative activity index.

I claim:

1. A process for the preparation of ethylene glycol and lower alkyl glycolate comprising the steps of contacting, in the vapor phase, hydrogen, with at least one of di(lower alkyl) oxalate in the presence of a hydrogenation catalyst comprising from about 1 to about 50% by weight, based on the total weight of the catalyst, of copper, and a silica carrier, wherein the silica carrier is characterized by a relative activity index of at least about 1.0, said relative activity index being defined by the formula, relative activity index = $1.38 + 0.39a + 0.76b + 0.001c + 0.35d - 0.39ab + 0.012bc + 0.003cd$, wherein a is defined as the nominal external surface area of a typical carrier particle (S), expressed in square millimeters per particle units, divided by the volume (V) of the same carrier particle, expressed in cubic millimeters per particle units minus 1.96 ((S/V) − 1.96); b is defined as the pore volume (P) of the carrier, expressed in cc/gram units, minus 0.84 (P − 0.84); c is defined as the average pore diameter (D), expressed in Angstrom units, minus 169 (D − 169); and d is defined as the macroporosity variable (M) minus 0.24 (M − 0.24), wherein the macroporosity variable is assigned a value of 1.0 if said carrier has at least about 20% of its pore volume associated with pores having a diameter of at least about 1000 Angstroms, and a value of zero if said carrier has less than about 20% of its pore volume associated with pores having a diameter of at least about 1000 Angstroms.

2. The process of claim 1 wherein said relative activity index is greater than about 1.25.

3. The process of claim 1 wherein said relative activity index is greater than about 1.50.

4. The process of claim 1 wherein said lower alkyl is methyl or ethyl.

5. The process of claim 1 wherein said carrier has a pore volume of about 0.4 cc/gram to 1.5 cc/gram.

6. The process of claim 1 wherein said carrier has a pore volume of about 0.7 to 1.5 cc/gram.

7. The process of claim 1 wherein said carrier has a pore volume of about 0.9 to 1.5 cc/gram.

8. The process of claim 1 wherein said carrier has an average pore diameter of about 25 to 600 Angstroms.

9. The process of claim 1 wherein said carrier has an average pore diameter of about 50 to 600 Angstroms.

10. The process of claim 1 wherein said carrier has an average pore diameter of about 125 to 600 Angstroms.

11. The process of claim 1 wherein said carrier has a nominal external surface area to volume ratio of about 0.5 to 5.0 $mm^{-1}$.

12. The process of claim 1 wherein said carrier has a nominal external surface area to volume ratio of about 0.75 to 5.0 $mm^{-1}$.

13. The process of claim 1 wherein said carrier has a nominal external surface area to volume ratio of about 1.0 to 4.0 $mm^{-1}$.

14. The process of claim 1 wherein said carrier has a surface area of about 50 $m^2$/gram to 600 $m^2$/gram.

15. The process of claim 1 wherein said carrier has a surface area of about 75 to 400 $m^2$/gram.

16. The process of claim 1 wherein said carrier has a surface area of about 100 to 300 $m^2$/gram.

17. The process of claim 1 wherein the pressure is between about 1 bar and 350 bars, the molar ratio of hydrogen to oxalate ester fed to the reaction zone between about 4:1 and 200:1, the temperature about 150° C. to 300° C., and the gas hourly space velocity about 2,000 $hr.^{-1}$ to 25,000 $hr.^{-1}$ and the liquid hourly space velocity about 0.1 $hr.^{-1}$ to 3.0 $hr.^{-1}$.

* * * * *